United States Patent [19]

Varner

[11] Patent Number: 5,792,209
[45] Date of Patent: Aug. 11, 1998

[54] OSTEOPOROSIS-RELIEF DEVICE

[76] Inventor: Lawrence Norman Varner, 5277 S. Boston St., Englewood, Colo. 80111

[21] Appl. No.: 625,996

[22] Filed: Apr. 1, 1996

[51] Int. Cl.[6] .............................. A61N 1/36; A61N 1/04
[52] U.S. Cl. .............................. 607/51; 607/50; 607/117; 600/13
[58] Field of Search ...................... 607/50, 51, 52, 607/115, 57, 117; 600/13

[56] References Cited

U.S. PATENT DOCUMENTS

| | | |
|---|---|---|
| 3,915,151 | 10/1975 | Kravs . |
| 5,191,880 | 3/1993 | McLeod et al. . |
| 5,217,009 | 6/1993 | Kronberg . |
| 5,267,939 | 12/1993 | Liboff et al. ........................... 607/52 |
| 5,413,596 | 5/1995 | Kronberg . |

*Primary Examiner*—William E. Kamm
*Assistant Examiner*—Carl H. Layno

[57] ABSTRACT

An apparatus provides relief from osteoporosis, through either prevention of its development or reversal of its presence, by utilizing a light-weight portable low intensity, low frequency electrical field specifically targeted for osteoporotic of hips and spine, thereby reducing the growing numbers of hip and vertebral fractures in our aging population. The apparatus is simple to utilize, safe, of inexpensive construction, convenient to use, and may be incorporated permanently within a specific designer line of clothing made for this purpose, or the device may be portable and adaptable to a variety of clothing which the wearer may choose, as that person's fashion preferences may dictate. The hip areas of the official pants are padded to absorb energy if the wearer accidentally falls onto either hip, decreasing the likelihood of a hip fracture. Electrode placements are discussed, for proper positioning of the electromagnetic fields; also addressed are the design of the clothing incorporating this osteoporosis-relief system, and the design of the spine electrode "envelopes".

9 Claims, 3 Drawing Sheets

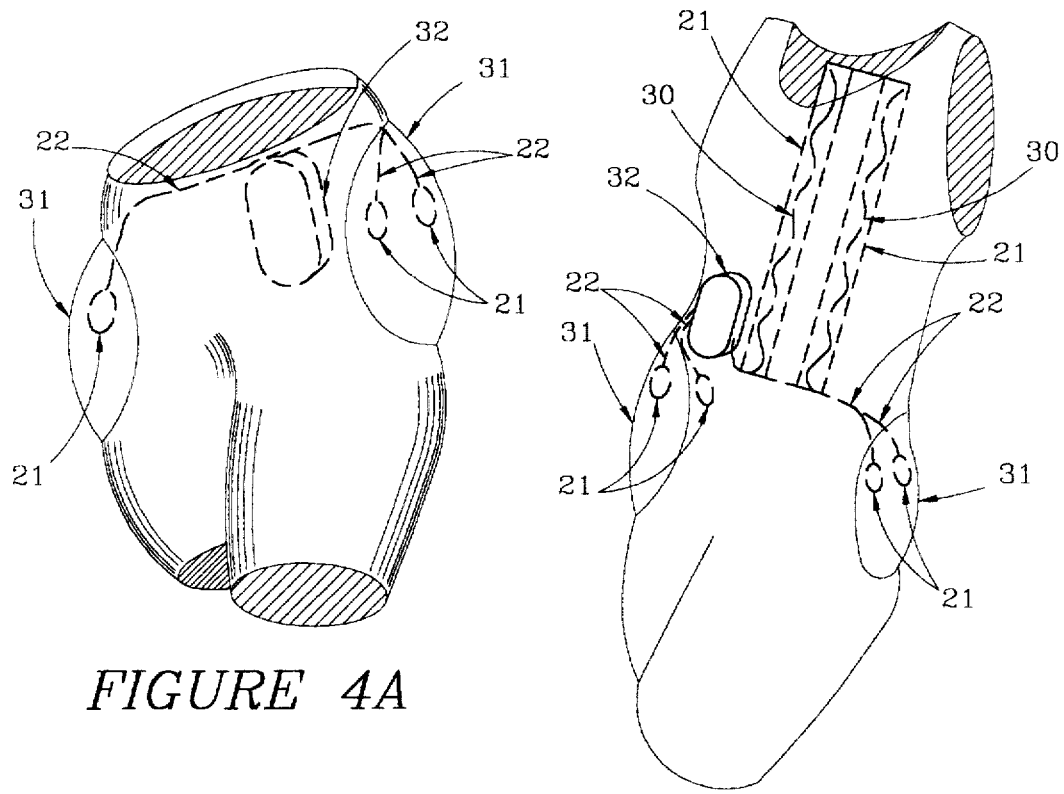
FIGURE 4A
FIGURE 4B
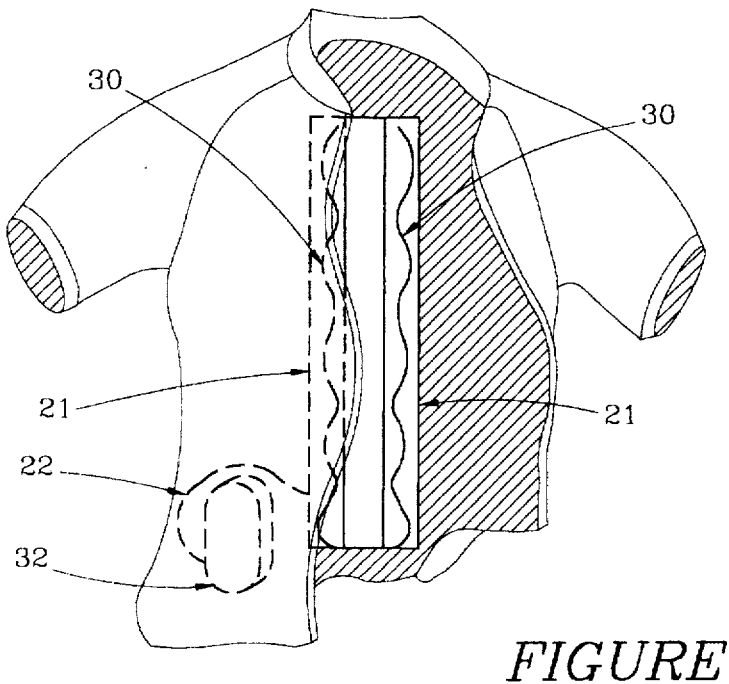
FIGURE 4C

OSTEOPOROSIS-RELIEF DEVICE

BACKGROUND OF THE INVENTION

A) Field of the Invention.

This invention relates in general to reversal and prevention of osteoporosis and prevention of osteoporosis-related spine fractures and hip fractures, and in particular, to low-frequency, low-voltage electromagnetic fields conveniently placed, in relationship to the bones at risk for fracture, to slow the progress of osteoporosis or reverse its development.

B) Description of Related Art and Prior Art.

"Osteoporosis" is a reduction in bone mass. Osteoporosis is a chronic disabling disorder, predominantly affecting the elderly white female population. As our population of "baby boomers" age, they are predisposed to development of osteoporosis and complications thereof. A 1986 pilot study showed that osteoporotic patients had a reduced quality of life when compared to aged-matched controls; their quality of life regressed with increasing severity of osteoporosis-related fractures. By the year 2020, about one half of the U.S. population will be over the age of 65, with a significant increase in osteoporosis-related fractures. Reaction times slow and proprioception (balance) problems increase after age 65, putting older adults at risk for more auto accidents and falls, often leading to broken hips. The life-time risk of any fracture of the hip, spine or distal forearm is almost 40% in white females and 13% in white males over 50 years of age. Today, there is an average of one fall per second in the United States, 30 million falls per year. 2,400 falls require hospitalization daily in the U.S. If an osteoporotic patient falls directly onto his or her side/hip, the risk factor for a hip fracture is increased times six. One fall in seven results in a fracture; these fractures are one of the foremost reasons that the elderly lose their independence and require nursing home care.

It is predicted that by the year 2050, projected numbers of hip fractures world wide will be 4.8 million females, and 1.8 million males. Of the males who break a hip, 40% will die within three months; the rest do not have a very good quality of life. Of the females, 20% die within three months, but of the 80% who survive, ½ never return to their usual activities of daily living (ADL). In a recent scientific paper by Dr. John 0. Mullen, M.D., of Huntington, W. Va., 312 consecutive surviving patients were evaluated one year after their hip fractures. 61% of these patients who could walk prior to fracturing their hip suffered a decrease in activity level and 63% were using more walking aides. Half of those who are outdoor-independent had now become "shut-ins". Among those who had been living alone, 39% became dependent upon their family. Nine percent of the patients who had been living alone or with a family prior to the hip fracture now resided in a nursing home. The financial impact of these fractures, by year 2050, will be astounding; even today, 10 billion dollars a year is spent in the U.S. alone for hip fractures. In 1986, a detailed study in the U.S. assessed direct medical costs of osteoporosis in women over 45, including costs of outpatient services, hospitalization and nursing home care (the latter two being the greatest contributors). The result in figures for total direct care came to $5.15 billion; a similar 1989 study showed expenditures had risen to over $6 billion. A pure economic analysis of the direct-medical burden of osteoporosis does not address indirect costs to patients, relatives or health care providers. Nor does it address additional peripheral issues such as "quality of life", disability, and socioeconomic factors. A 1994 study titled "Costs and Health Effects of Osteoporotic Fractures" states that among white U.S. women aged 45 or older, an estimated 5.2 million hip, spine and forearm fractures are expected in the next 10 years; this includes 2 million person-years of fracture-related functional impairment. Although the costs of osteoporosis-related hip fractures seems accurate here, not so for vertebral (spine) fractures, which have a varied clinical presentation. In the osteoporotic spine, simply coughing, sneezing, or lifting groceries can cause a vertebral body compression fracture; of females over 80, one-half has one or more vertebral body fractures.

Although primary osteoporosis is the most common type of osteoporosis, there are other causes of "secondary osteoporosis", such as steroid use, or malignancy. Patients is taking over 7.5 mgs of steroid per day will lose bone mass over time, becoming osteoporotic. Breast cancer patients on Tomaxafin will also lose bone mass at the hips, weakening them for potential hip fractures.

Medical science has developed many partial solutions to reversing/treating osteoporosis, including nasal calcitonin, and many oral drugs, including biphosphonates (Fosamax, Didronel), estrogen therapy, androgens, growth factors, calcium and vitamin D, sodium fluoride, vitamin K, Zeolite, and Ralaxatene. Most of these medicines cost at least $60 a month, a significant long-term consideration; some cause esophagitis and compliance is difficult for some, especially with estrogen-replacement, for fear of developing related breast cancer or fatal ovarian cancer. A 1987 survey showed that up to 30% of American women given an estrogen prescription never filled it. Of those who did, one-fifth quit taking the hormone within 9 months; others went on and off the medication. Also, some drug interactions occur which are not helpful; for example, although taking calcium in ones diet is very important in treatment of osteoporosis, if calcium supplement is taken with Fosamax, (a new "drug of choice"), this calcium supplement blocks the action of that drug. Routine compliance with almost any oral medication becomes somewhat difficult over time, with issues of GI intolerance, other side-affects of the medication, and ongoing costs playing a part.

Recent animal studies at State University of New York, Stony Brook, and Emory University have shown that electrical fields below 10 uV/cm, at low frequencies such as 15 Hz are similar to those electrical fields produced in bone by normal daily functional activity, and an experimental sinusoidal wave field initiated more new bone formation than did stronger, more complex pulsed electromagnetic fields (P.E.M.F.), at only 0.1% of the electrical energy, suggesting this is an extremely safe way to promote bone mass in the osteoporotic individual.

Although there are portable electrical devices on the present market designed for health purposes, these are intended for muscle stimulation (The Muscle Max EMS"—Smith and Nephew Donjoy Inc.), for surface E.M.G. monitoring ("Muscle Sense" by Donjoy), or for fracture healing (EBI Orthopak and orthologic); none have yet been devised for the purposes intended herein, to be utilized for treatment or prevention of osteoporosis.

Osteoporosis can be diagnosed as a reduction of bone mass before a fracture actually occurs, by using the latest technology called "duel x-ray absorptiometry ("DXA"); fortunately, the cost of this expensive study is slowly decreasing. If a person has a low bone mass, one has 7.5 times the chance of developing fractures of these weakened bones. Decreased bone mass predicts the probability of a fracture better than serum cholesterol levels predict a possible heart attack, or increased blood pressure predicts a possible stroke. The natural history of development of primary osteoporosis, and the inherent safety of my invention, precludes the need for routine repeated and costly diagnostic studies to formally make this diagnosis; the preventive effects of my invention may consistently benefit the entire population at risk, on an ongoing basis, with no significant or harmful known side-effects. Ideally, my invention is part of a preventive health program which includes oral calcium and vitamin D, along with weightbearing exercises.

One only needs to consider the astounding costs to society if 60% of the elderly in the year 2020 needed nursing home care or home-health care! Osteoporosis interventions that can reduce the need for fracture-related extended nursing home care will be particularly cost-effective, as will effective measures in females aged 65–84, who are expected to experience the largest number of fractures, and fracture-care costs in the next 10 years. "Prevention" of osteoporosis-related fractures will be most cost-efficient, reducing the $45.2 billion estimate of total direct-medical costs expected in the next 10 years for hip, spine and forearm fractures, alone. However, no non-medicinal, electrical device is known for safely treating or preventing osteoporosis in an effective, reliable, and inexpensive manner; whatever the precise merits features and advantages of the above-sited references none of them achieves or fulfills the purposes of my present invention.

SUMMARY OF THE INVENTION

The principal object of the present invention is to provide a light-weight portable low-intensity, low-frequency electromagnetic field to prevent or reverse osteoporosis of hips and spines in the older individual, thereby reducing the growing numbers of hip and vertebral fractures.

It also is an object of the present invention to provide such a device and system which is simple, safe, of inexpensive construction, and convenient to use, for our aging population.

Another object is to provide a light-weight system which may be permanently affixed to a specific designer clothing line, or which may be portable and therefore adapted to a variety of clothing which its wearer may choose, as that individuals fashion preferences may dictate.

A further object is to pad the hip areas of the official designers pants, to absorb energy if one accidentally falls directly onto either hip, to reduce the likelihood of a fall-related hip fracture.

The foregoing objects can accomplished by providing a small light-weight portable battery-operated power source which provides a low intensity, low frequency electromagnetic field to the hips and spine, through electrodes which are placed anatomically correctly, and are connected to the power source via thin wires. The batteries and electrodes may be built into an outfit of cotton/polyester/lycra/spandex blend, the snug but comfortable material being necessary to assure consistent and reproducible electrode placement; or the entire electromagentic field (E.M.F.) system may be easily adapted to the wearer's choice of wardrobe of similar fabric/material as the official fabrics.

BRIEF DESCRIPTION OF THE DRAWINGS

FIG. 4. A, B, C, show examples of the snug-fit clothing fashion line, including shorts 4A, a dress 4B, and a zippered vest 4C.

DETAILED DESCRIPTION

Figure 1A:
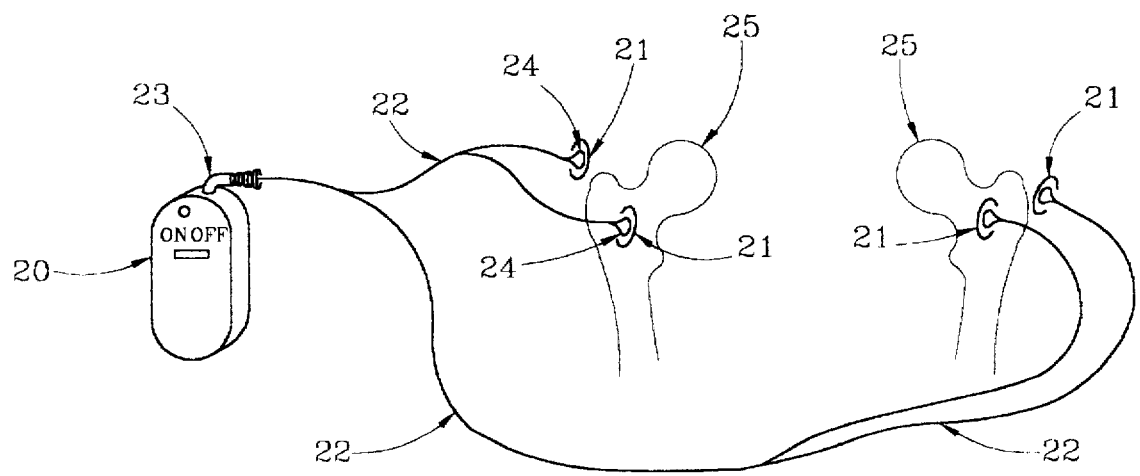
FIG. 1. Illustrates a preferred embodiment of the osteoporosis-relief device, showing positioning of the hip electrodes in relation to the proximal femur FIG. 1A, and positioning of the spinal electrodes in relationship to the spine FIG. 1B.
Figure 1B:
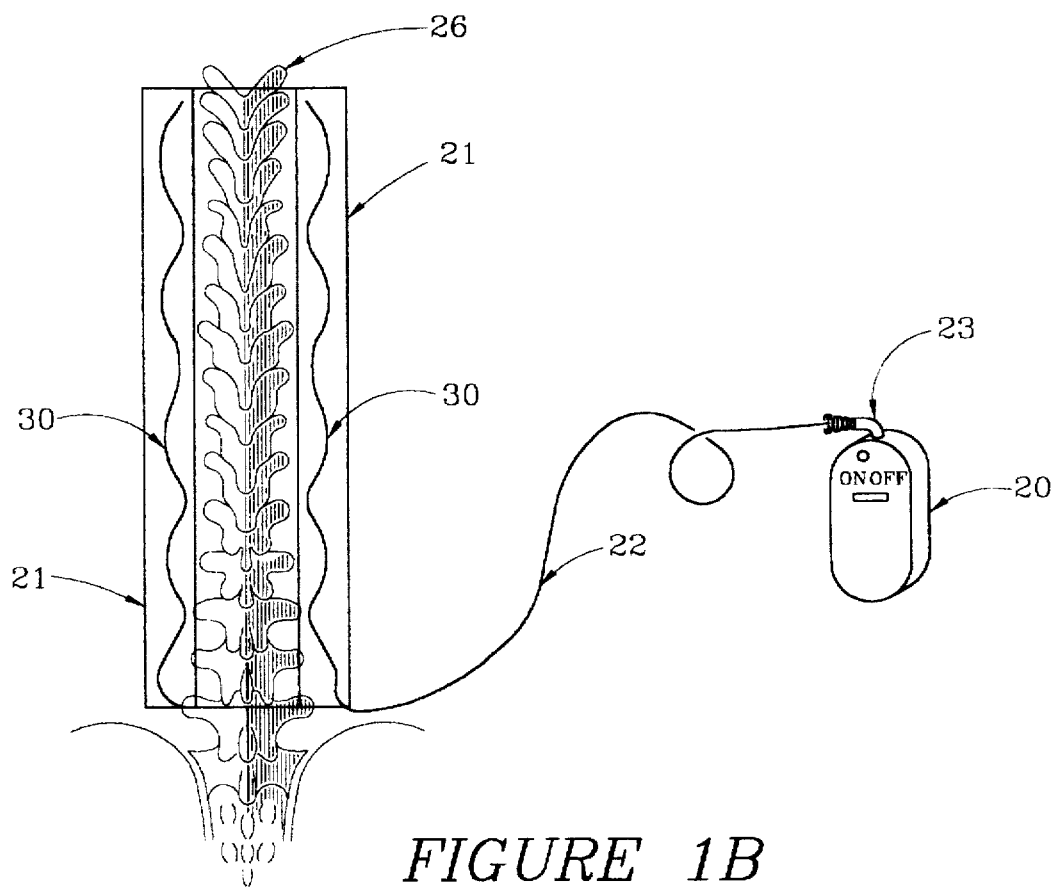

Refer now to figure one, A & B which is an over-all drawing of a preferred embodiment of the invention, the osteoporosis-relief device; in accordance with the present invention, and as shown in the drawings, the device comprises a small light-weight portable battery-operated power source 20 weighing three ounces or less, housed in a strong molded plastic or synthetic control pack also containing a microchip means for controlling an appropriate wave form and a coil affecting an electromagnetic field, appropriate skin lead "electrodes" 21 with wires 22 connecting, by coaxial plugs 23 or pigtails, to a battery power-source and by snaps 24 to a skin leads, the latter which will be placed about both hips 25, FIG. 1-A, and thoracic and lumbar spine 26, FIG. 1-B to transmit a low-intensity, 10 uV/cm or less, low-frequency, 15 Hz or in the range of 10–100 Hz, sinusoidal electromagnetic wave signal, or other appropriate wave form or signal to be determined, to the osteoporotic bone of the hips and the spine for approximately one hour per day, or a variation thereof, for the purpose of decreasing the amount of osteoporosis present, to stimulate bone mineralization. The osteoporosis-relief device has a power system 20 comprising removable or permanently-incorporated rechargeable batteries, or disposable batteries or lithium wafer batteries or have AC power adaptability, solar cell power capabilities, or other power sources of a convenient, reliable, compact nature, and has various micro chips which determine a variety of predetermined wave forms, and has various coils with predetermined strengths of electromagnetic fields, including frequency, and intensity of electrical impulses, and will have an on-off switch with a power light which illuminates when the control pack is turned on. Whatever the power source 20, it is connected via wires 22 to the electrodes 21 which are placed specifically at the hips 25 or spine 26.

Figure 2:
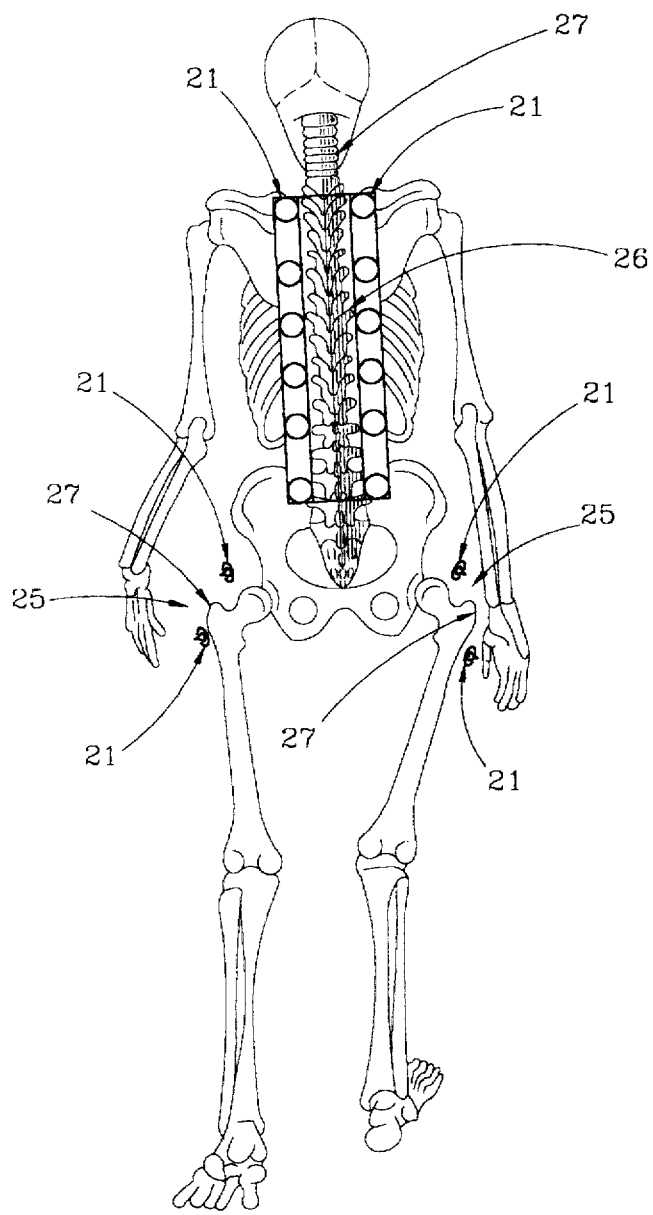
FIG. 2. Shows a posterior view of the human anatomy, with the electrodes in proper position.

A pair of electrodes 21 are placed over each hip 25, per FIG. 2, approximately six inches apart, one three inches to the front of the tip of the greater trochanter 27 of the hip, and the second electrode is three inches behind this same tip of the greater trochanter 27 of the hip. The electrodes 21, per FIG. 2 which are to be placed along the spine, are comprised of two thin narrow strips of plastic, cellophane, thin cloth, or other synthetic or natural material, each electrode strip measuring approximately 15 inches long, and one inch wide, containing a series of approximately six round skin electrodes/leads, which directly contact the skin, each of the six leads being approximately one inch in diameter, and placed equal distance apart throughout the entire electrode strip, and the strip backing having velcro tabs or other means to easily connect, and disconnect the electrode strip on the inside of the selected clothing, to allow electrode removal during laundry. These electrode strips are placed longitudinally along the spine 26, approximately ¾ inch on either side of the midline of the spine 26, starting two inches distal to the "vertebra prominens" (the consistently prominent C7 spinous process), and running distally from that point 27. For proper function, the contact surfaces of the electrodes must be contacting the skin, not faced away from the skin.

Figure 3:
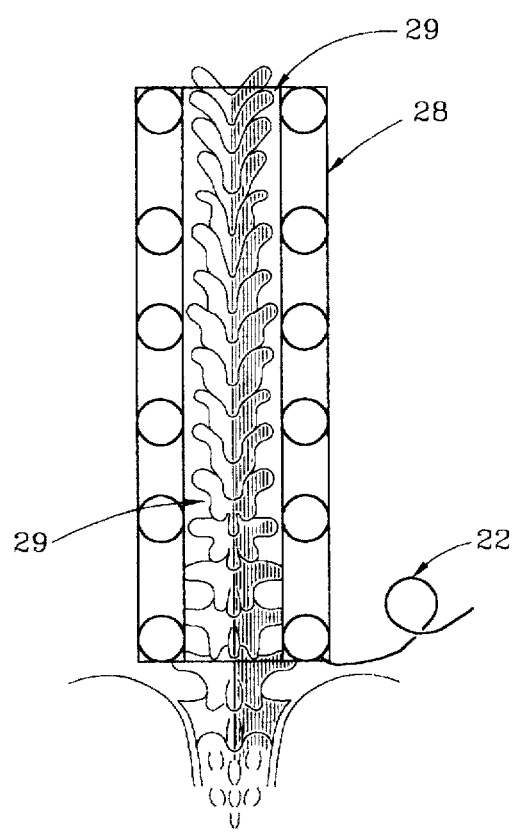
FIG. 3. Illustrates the spine electrodes as an alternative embodiment, with a single envelope for ease of electrode placement.

The above-described two narrow electrode strips 21 may be combined, per FIG. 3, to form one single larger thin, lightweight envelope 28 approximately 3½"×15", for ease of user placement into ones own clothing, whereby two strips of electrodes are connected by an electrode-free or wire-free strip 29 of approximately one and a half inches in width, with this 1-½ inch center longitudinal strip being centered over the spinous processes of the thoracic and lumbar spine. FIG. 1-B shows a variation upon this single-envelope spine electrode model, which is a single pair of long thin serpentine inductions coils 30, approximately 15 inches long each, instead of 6 separate interconnected individual skin electrodes on either side of the spine 26 with each coil running longitudinally, ¾ inches on either side of the spine midline, and then connecting to the control pack through a single lead cable, by a small coaxial plug.

The above system is to be manufactured and incorporated into a special snug-fit clothing fashion line, per FIGS. 4 A, B, C, comprised of shorts FIG. 4A, pants, or full-length tights, dress FIG. 4B skirt, shirt or vest FIG. 4C, made of lycra/spandex or cotton/polyester/lycra blend or other synthetics/natural fiber materials with memory and stretch, to assure reasonable and consistent placement of the electromagnetic field electrodes over the hip and spine regions intended to receive the safe low-intensity current. The shorts FIG. 4A pants, or dress, FIG. 4B may incorporate energy-absorbing removable or permanently-placed pads 31 over both left and right hip areas (greater trochanter), comprising pads of varied size and thickness to best serve different size wearers, and are constructed of foam or other synthetic or natural materials, the purpose of said pads being to decrease the force of impact and decrease the likelihood of a hip fracture if wearer accidentally falls directly onto the lateral aspect of either hip. If the direction of a fall is onto either side, directly onto the hip, the risk factor of sustaining a hip fracture is increased by six times; hence the hip pads. These pads 31 may also relieve any minimal pressure which might otherwise occur from the leads 21, if the user is laying on either hip. The official clothing fashion line has have built-in pockets 32 to accommodate the small control-pack, with the lead wires connecting to these pockets for ease of connection to the control-pack by a small coaxial plug, to allow easy disconnection and reconnection of lead wires to the control pack for ease of maintenance, battery change, and laundry of outfit.

A template may be available for properly placing the electrodes if the wearer chooses to use their own appropriate personal clothing set, to "retrofit" the electromagnetic field system, including the electrodes, leads, and power source/control-pack, to their own clothing. The osteoporosis-relief device 20 is available independently of manufacturers pre-selected clothes, with a belt and pouch to hold the battery/control-pack and may be utilized without the prescribed shorts or pants, shirt or vest, to instead be adapted to ones own personal choice of wardrobe by using placement templates and adhesive and velcro or other means of attachment inside for the leads, providing that the personal choice of clothing to which the system is adapted is close-fitting, to assure consistent lead placement with relation to the hips and spine, for the intended bone-stimulation process. Bicycle shorts and tops or knit dresses of cotton/spandex combination material are examples of appropriate clothing to which this system is adaptable.

It is believed the invention operates as follows: Normal living bone has a naturally-occurring very low-energy electrical field/current within it when under any "load" or stress such as walking, running or lifting; the muscle contractions which occur with such activities are felt to generate these low amplitude, low frequency, 10 Hz to 100 Hz, electrical energies, which indirectly affect "osteoregulation", or the body's ability to make new bone. This "piezoelectric potential", the term for the very low-frequency and low-intensity electrical field normally found in bone, has been experimentally reproduced, and bone reabsorption, and related weakening that normally accompanies disuse has been prevented or even reversed by artificially reproducing this electrical field externally. Recent animal studies have shown that electrical fields below 10 uV/cm, at low frequencies such as 15 Hz, are very similar to these natural "electrical fields" which are produced in bone by normal daily functional activity. An experimental sinusoidal wave field also was much better than a complex "pulsed electromagnetic field" (PEMF), at initiating more new bone formation in experimental animals, using only 0.1% of the electrical energy necessary to accomplish these improved results; This strongly suggests that my device is an extremely safe way to promote bone mass in the osteoporotic individual. Most aging humans, throughout their lives, normally lose 1½ inches in height due to spine disc degeneration and a related collapse in their spine; this device may be safely used on all post-menopausal females or aging males, who lose over 1½ inch in height due to osteoporotic compression fractures. The device may also be used in all post-menopausal females without the expensive diagnostic study, "duel x-ray absorptiometry" (DEXA), which has been utilized to justify the ongoing expensive, and sometimes risky medication treatment programs currently available. This device may also be beneficial for patients who are at long-term bed rest, who are at risk for developing "disuse osteoporosis" with subsequent accidental fractures which may occur during daily nursing care. Currently it is suggested that the device needs to be turned "on" for only a minimum of approximately one hour per day and could be worn by the user during daytime activities, or at night, while asleep.

The foregoing description of the preferred embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description but rather by the claims appended hereto.

I claim:

1. An osteoporosis-relief device comprising a small lightweight portable battery-operated power source, weighing three ounces or less, housed in a strong molded plastic or synthetic control pack also containing a microchip means for controlling an appropriate wave form, and a coil affecting an electromagnetic field, appropriate skin lead electrodes with wires connecting by coaxial plugs or pigtails to a battery power-source and by snaps to skin leads, the latter which will be placed about both hips and thoracic and lumbar spine, to transmit a low-intensity, 10 uV/cm or less, low-frequency, 15 Hz or in the range of 10–100 Hz, sinusoidal electromagnetic wave signal, or other appropriate wave form or signal to be determined, to the osteoporotic bone of the hips and the spine for approximately one hour per day, or a variation thereof, for the purpose of decreasing the amount of osteoporosis present, to stimulate bone mineralization.

2. The osteoporosis-relief device of claim 1 has a power system comprising removable or permanently-incorporated rechargeable batteries, or disposable alkaline batteries, or lithium wafer batteries or have AC power adaptability, solar cell power capabilities, or other power sources of a convenient, reliable, compact nature, and has various micro chips which determine a variety of predetermined wave forms, and has various coils with predetermined strengths of electromagnetic fields, including frequency, and intensity of electrical impulses, and will have an on-off switch with a power light which illuminates when the control pack is turned on.

3. The electrodes of claim 1, which are to be placed along the spine, are comprised of two thin narrow strips of plastic, cellophane, thin cloth, or other synthetic or natural material, each electrode strip measuring approximately 15 inches long, and one inch wide, containing a series of approximately six round skin electrodes/leads, which directly contact the skin, each of the six leads being approximately one inch in diameter, and placed equal distance apart throughout the entire electrode strip, and the strip backing having velcro tabs or other means to easily connect, and disconnect the electrode strip on the inside of the selected clothing, to allow electrode removal during laundry.

4. The two narrow electrode strips of claim 3 may be combined into one piece, comprising one single larger thin, lightweight envelope approximately 3½"×15", for ease of user placement into ones own clothing, whereby two strips of electrodes are connected by an electrode-free strip of approximately 1½ inches; with this 1½ inch centered longitudinal strip being centered over the spinous processes of the thoracic and lumbar spine midline.

5. A variation upon the single envelope spine electrode model of claim 4 is comprising a single pair of long thin serpentine, induction coils approximately 15 inches long each, instead of 6 separate interconnected individual skin electrodes on either side of the spine, with each coil running longitudinally, ¾ inches on either side of the spine midline, and then connecting to the control pack through a single lead cable, by a small coaxial plug.

6. The osteoporosis-relief device of claim 1 is to be manufactured and incorporated into a special comfortable snug-fit clothing fashion line comprising shorts, pants or full-length tights, dress, skirt, shirt or vest, made of lycra/spandex or cotton/polyester/lycra blend or other synthetic/natural fiber materials with memory and stretch, to assure reasonable and consistent placement for the electromagnetic field electrodes over the hip and spine regions intended to receive the safe low-intensity current.

7. The shorts or pants referred to in claim 6 incorporate energy-absorbing removable or permanently -placed pads over both left and right hip areas (greater trochanter), comprising pads of varied size and thickness, to best serve different sized wearers, and constructed of foam or other synthetic or natural materials, the purpose of said pads being to decrease the force of impact and decrease the likelihood of hip fracture if wearer accidentally falls directly onto the lateral aspect of either hip.

8. The official clothing fashion line of claim 6 has built-in pockets to accommodate the small control-pack, with the lead wires connecting to these pockets for ease of connection to the control-pack by a small coaxial plug, to allow easy disconnection and reconnection of lead wires to control pack for ease of maintenance, battery change or charge, and laundry of outfit.

9. The osteoporosis-relief device system in claim number 1 is available independently of manufacturers pre-selected clothes, with a belt and pouch to hold the battery/control-pack and may be utilized without the prescribed shorts or pants, shirt or vest, to instead be adapted to ones own personal choice of wardrobe by using placement templates and adhesive and velcro or other means of attachment inside for the leads, providing that the personal choice of clothing to which the system is adapted is close-fitting, to assure consistent electrode/lead placement with relation to the hips and spine, for the intended bone-stimulation process.

* * * * *